United States Patent
Kramer

(10) Patent No.: US 10,004,233 B2
(45) Date of Patent: Jun. 26, 2018

(54) RELATING TO TREATMENT OF WATER

(71) Applicant: BWA WATER ADDITIVES UK LIMITED, Manchester (GB)

(72) Inventor: Jeffrey Frank Kramer, Tucker, GA (US)

(73) Assignee: BWA Water Additives UK Limited, Manchester, Greater Manchester (GB)

(*) Notice: Subject to any disclaimer, the term of this patent is extended or adjusted under 35 U.S.C. 154(b) by 0 days. days.

(21) Appl. No.: 14/872,399

(22) Filed: Oct. 1, 2015

(65) Prior Publication Data
US 2017/0094975 A1 Apr. 6, 2017

(51) Int. Cl.
A01N 57/20 (2006.01)
C02F 1/50 (2006.01)
A01N 43/76 (2006.01)

(52) U.S. Cl.
CPC ............ *A01N 57/20* (2013.01); *A01N 43/76* (2013.01); *C02F 1/50* (2013.01); *C02F 2303/04* (2013.01); *C02F 2303/20* (2013.01)

(58) Field of Classification Search
CPC ........ A61K 31/66; A01N 57/20; A01N 43/76; C02F 1/50
USPC ......................................................... 514/75
See application file for complete search history.

(56) References Cited

U.S. PATENT DOCUMENTS

| | | |
|---|---|---|
| 3,281,365 A | 10/1966 | Moedritzer |
| 4,835,143 A | 5/1989 | Donofrio et al. |
| 4,874,526 A | 10/1989 | Grade et al. |
| 5,063,213 A | 11/1991 | Whitekettle et al. |
| 5,063,214 A | 11/1991 | Whitekettle et al. |
| 5,063,218 A | 11/1991 | Whitekettle et al. |
| 5,102,874 A | 4/1992 | Lintner et al. |
| 5,376,731 A | 12/1994 | Kerr et al. |
| 5,741,757 A | 4/1998 | Cooper et al. |
| 6,241,898 B1 | 6/2001 | Wright et al. |
| 6,419,879 B1 | 7/2002 | Cooper et al. |
| 6,478,972 B1 | 11/2002 | Shim et al. |
| 6,669,904 B1 | 12/2003 | Yang et al. |
| 6,926,836 B2 | 8/2005 | Fidoe et al. |
| 2005/0061753 A1 | 3/2005 | Dickinson |
| 2006/0032823 A1 | 2/2006 | Harrison et al. |
| 2006/0113251 A1 | 6/2006 | McGuire et al. |
| 2007/0012632 A1 | 1/2007 | Simons |
| 2008/0248555 A1 | 10/2008 | Lee |
| 2010/0200239 A1 | 8/2010 | Aften |
| 2010/0226874 A1 | 9/2010 | Kramer et al. |
| 2010/0286096 A1* | 11/2010 | Yin ................. A01N 57/20 514/126 |
| 2011/0174492 A1 | 7/2011 | Robb et al. |
| 2012/0024794 A1 | 2/2012 | Fischmann |
| 2012/0073821 A1 | 3/2012 | Holtsclaw et al. |
| 2012/0178722 A1 | 7/2012 | Yin |
| 2012/0285693 A1 | 11/2012 | Mirakyan et al. |
| 2014/0030306 A1 | 1/2014 | Polizzotti et al. |
| 2014/0194335 A1 | 7/2014 | Gu et al. |

FOREIGN PATENT DOCUMENTS

| | | |
|---|---|---|
| EP | 0479465 A2 | 4/1992 |
| EP | 0681995 A1 | 10/1994 |
| GB | 2354771 A | 4/2001 |
| JP | 10273408 A | 10/1998 |
| JP | 2010167320 | 5/2010 |
| WO | 9104668 A1 | 4/1991 |
| WO | 0142145 A1 | 6/2001 |
| WO | 03031347 A1 | 4/2003 |
| WO | 03073848 A1 | 12/2003 |
| WO | 2005123607 A1 | 12/2005 |
| WO | 2010100470 A2 | 9/2010 |
| WO | 2013032961 A1 | 3/2013 |

OTHER PUBLICATIONS

U.S. Appl. No. 14/513,693, filed Oct. 14, 2014, Kramer.
U.S. Appl. No. 14/513,735, filed Oct. 14, 2014, Kramer.
U.S. Appl. No. 14/513,768, filed Oct. 14, 2014, Kramer.
U.S. Appl. No. 14/673,419, filed Mar. 30, 2015, Kramer et al.
U.S. Appl. No. 14/840,674, filed Aug. 31, 2015, Kramer.
U.S. Appl. No. 14/870,951, filed Sep. 30, 2015, Kramer.
U.S. Appl. No. 14/874,686, filed Oct. 5, 2015, Kramer et al.
U.S. Appl. No. 14/878,240, filed Oct. 8, 2015, Kramer et al.
BWA Water Additives, "Product Label for Bellacide© 303," http://www.kellysolutions.com/erenewals/documentsubmit/KellyData%5COK%5Cpesticide%5CProduct%20Labe1%5C83451%5 C83451-20%5C83451-20 Bellacide 303 6 16 2011_2_54_43_PM.pdf.
BWA Water Additives, "Product Information for Bellacide© 303—Multi-purpose Non-oxidizing Biocide for Industrial Water Systems," http://www.wateradditives.com/Repository/Files/BWA_Bellacide_303_GP_WF_-_AsiaPac_O.pdf.
BWA Water Additives, "Technical Data for Bellacide© 303—Multi-purpose Non-oxidizing Biocide for Industrial Water Systems," http://www.wateradditives.com/Repository/Files/BWA_Bellacide_303_TI_WF_AsiaPac.pdf.
Kull, F C. et al., "Mixtures of Quaternary Ammonium Compounds and Long-chain Fatty Acids as Antifungal Agents," Applied Microbiology, Nov. 1961, pp. 538-541, vol. 9, No. 6, The American Society for Microbiology by the Williams & Wilkins Company, Baltimore, MD.
May, Oscar W., "Polymeric Antimicrobial Agents," Disinfection, Sterilization, and Preservation, Chapter 18, Jan. 1, 1991, pp. 322-333, Philadelphia, Lea & Febiger, US.
Rembaum, A, "Biological Activity of Ionene Polymers," Applied Polymer Symposium, 1973, pp. 299-317, No. 22, J. Wiley & Sons, Inc., New York, NY.

(Continued)

Primary Examiner — Yong Chu
(74) Attorney, Agent, or Firm — McNees Wallace & Nurick LLC

(57) ABSTRACT

The present invention relates to water treatment. In one embodiment there is provided a method of treating an aqueous system to inhibit growth of one or more micro-organisms therein and/or to reduce the number of live micro-organisms therein. The method comprises adding treatment agents to said aqueous system and wherein said treatment agents comprise: (a) a phosphonium compound; and (b) an oxazolidine compound.

12 Claims, No Drawings

(56) References Cited

OTHER PUBLICATIONS

U.S. Appl. No. 12/399,300, Final Office Action dated Feb. 23, 2016, 14 pages.
U.S. Appl. No. 14/513,693, Non-Final Office Action dated Feb. 26, 2016, 11 pages.
Giri, Jitendra et al., "Effluents from Paper and Pulp Industries and their impact on soil properties and chemical composition of plants in Uttarakhand, India," Journal of Environment and Waste Management, May 2014, pp. 026-032, vol. 1, No. 1, www.premierpublishers.org.
Jeffrey F. Kramer, et al. A New High Performance Quaternary Phosphonium Biocide for Microbiological Control in Oilfield Water Systems, Paper No. 08660, NACE International Corrosion 2008 Conference & Expo, 2008.
Yumi A. Warren, et al. Biochemical Differentiation and Comparison of Desulfovibrio Species and Other Phenotypically Similar Genera, Journal of Clinical Microbiology, Aug. 2005, p. 4041-4045.
Jonathan P. Zehr, Microbes in Earth's Aqueous Environments, Frontiers in Microbiology, Opinion Article, Published: Jul. 20, 2010.

\* cited by examiner

RELATING TO TREATMENT OF WATER

FIELD OF THE INVENTION

The present invention relates to water treatment, particularly though not exclusively, to methods of treating aqueous systems to inhibit growth of micro-organisms.

BACKGROUND TO THE INVENTION

The presence and growth of micro-organisms in aqueous systems, especially in industrial water systems, is a concern. Examples of industrial water systems where micro-organisms are a concern include cooling water systems, pulping and papermaking systems and oil and gas field water systems.

The presence of micro-organisms in industrial water systems may result in the formation of deposits on system surfaces. These deposits or slime can give rise to various problems. In cooling water systems, slime may restrict water flow, reduce heat transfer efficiency, cause corrosion and may be aesthetically unappealing especially if algae are present due to their visible green pigmentation. Corrosion can also occur in industrial water systems in the absence of visible slime through the action of micro-organisms.

In pulp and paper mill systems, slime formed by micro-organisms may cause fouling, plugging, or corrosion of the system. The slime may also break loose and become entrained in the paper produced causing blemishes, holes, tears, and odour in the finished product. The end result may therefore be unusable product and wasted output.

Slime can also be a problem in oil and gas field water systems and may cause energy losses due to increased fluid frictional resistance, formation plugging and corrosion. The slime may harbour a mixture of aerobic and anaerobic bacteria that are responsible for the production of hydrogen sulfide gas. The hydrogen sulfide may cause souring of oil and gas which may reduce the quality of these products and increase treatment costs.

*Pseudomonas aeruginosa* bacteria are commonly present in air, water and soil. These bacteria continually contaminate open cooling water systems, pulping and papermaking systems and oil and gas field water systems and are among the most common slime formers. Slime may be viewed as being a mass of cells stuck together by the cementing action of the gelatinous secretions around each cell. The slime entraps other debris, restricts water flow and heat transfer and may serve as a site for corrosion.

*Chlorella vulgaris* algae are also commonly present in air, water and soil. These algae continually contaminate open cooling water systems and their growth turns the water and surfaces in these systems green. They also provide a food source for bacteria, which can stimulate slime formation, and protozoa which can harbour the pathogenic bacterium *Legionella pneumophila*.

A known method of controlling microbial growth in aqueous systems is to use biocides. While biocides are known to inhibit microbial growth the biocidal effect is generally of limited duration. The effectiveness of known biocides may be rapidly reduced as a result of exposure to negative influences. Negative influences may include temperature, pH or reaction with ingredients present in the system which neutralizes their biocidal effect. Therefore, the use of such biocides may involve continuous or frequent addition and their application at multiple sites or zones in the system to be treated. The cost of the biocide treatment and the labour costs associated with the application of known biocides may therefore be significant.

Known biocides are also highly toxic in the quantities known to be required for effective control of microbial populations. As a result, the amount of biocides that can be safely discharged into the environment may be limited by environmental regulations. Therefore, the need exists for improved methods for controlling microbial growth in aqueous systems.

As noted above, known biocides have a number of limitations including the large quantities of biocides which typically have to be used to achieve the desired biocidal effect and the potential harmful effects on the environment of biocides and therefore reducing the amount necessary for control and thus the quantity released to the environment has many benefits.

Accordingly, the present invention aims to address at least one disadvantage associated with the prior art whether discussed herein or otherwise.

SUMMARY OF THE INVENTION

According to the present invention there is provided a method of treating an aqueous system as set forth in the appended claims. Other features of the invention will be apparent from the claims, and the description which follows.

According to a first aspect of the present invention there is provided a method of treating an aqueous system to inhibit growth of one or more micro-organisms therein and/or to reduce the number of live micro-organisms therein, wherein the method comprises adding treatment agents to said aqueous system and wherein said treatment agents comprise:
(a) a phosphonium compound; and
(b) an oxazolidine compound.

Suitably, the oxazolidine compound is selected from the group consisting of oxazolidines and oxazolidine derivatives. Suitably, the oxazolidine compound comprises an oxazolidine. Suitably, the oxazolidine compound consists of an oxazolidine. Suitably, the oxazolidine compound comprises an oxazolidine derivative. Suitably, the oxazolidine compound consists of an oxazolidine derivative.

Suitably, the oxazolidine compound comprises a methyloxazolidine. Suitably, the oxazolidine compound consists of a methyloxazolidine. Suitably, the oxazolidine compound comprises a dimethyloxazolidine. Suitably, the oxazolidine compound consists of a dimethyloxazolidine. Suitably, the oxazolidine compound comprises 4,4-dimethyloxazolidine (also known as DMO). Suitably, the oxazolidine compound consists of 4,4-dimethyloxazolidine.

Suitably, the method comprises adding a phosphonium compound as a phosphonium compound composition. The method may comprise adding a phosphonium composition comprising one or more phosphonium compounds and water. The method may comprise adding a phosphonium composition comprising a single phosphonium compound and water.

Suitably, the method comprises adding an oxazolidine compound as an oxazolidine composition. The method may comprise adding an oxazolidine composition comprising an oxazolidine compound and water. The method may comprise adding an oxazolidine composition comprising one or more oxazolidine compounds and water. The method may comprise adding an oxazolidine composition comprising a single oxazolidine compound and water.

The oxazolidine composition may comprise an oxazolidine and water. The oxazolidine composition may consist of an oxazolidine and water. The oxazolidine composition may comprise a methyloxazolidine and water. The oxazolidine composition may consist of a methyloxazolidine and water. The oxazolidine composition may comprise a dimethyloxazolidine and water. The oxazolidine composition may consist of a dimethyloxazolidine and water. The oxazolidine composition may comprise 4,4-dimethyloxazolidine and water. The oxazolidine composition may consist of 4,4-dimethyloxazolidine and water. The oxazolidine composition may comprise 4,4-dimethyloxazolidine as the sole oxazolidine compound.

Suitably, the method comprises treating an aqueous system such that 4,4-dimethyloxazolidine comprises greater than 50% of the total oxazolidine compound(s) added to the aqueous system. Suitably, the method comprises treating an aqueous system such that 4,4-dimethyloxazolidine comprises greater than 90% of the total oxazolidine compound(s) added to the aqueous system, for example 99% or greater.

Suitably, the method comprises treating an aqueous system such that 4,4-dimethyloxazolidine comprises greater than 50% of the total oxazolidine compound(s) present in the aqueous system. Suitably, the method comprises treating an aqueous system such that 4,4-dimethyloxazolidine comprises greater than 90% of the total oxazolidine compound(s) present in the aqueous system, for example 99% or greater.

Suitably, the method employs 4,4-dimethyloxazolidine as the only oxazolidine compound (b).

Suitably, there is provided a method of treating an aqueous system to inhibit growth of one or more micro-organisms therein and/or to reduce the number of live micro-organisms therein, wherein the method comprises adding treatment agents to said aqueous system and wherein said treatment agents comprise:
(a) a phosphonium compound; and
(b) 4,4-dimethyloxazolidine.

Suitably, the method comprises treating an aqueous system to inhibit growth of anaerobic bacteria and/or to reduce the number of live anaerobic bacteria therein. Suitably, the method comprises treating an aqueous system to inhibit growth of facultative anaerobic bacteria and/or to reduce the number of live facultative anaerobic bacteria therein. Suitably, the method comprises treating an aqueous system to inhibit growth of aerobic bacteria and/or to reduce the number of live aerobic bacteria therein.

Suitably the aqueous system comprises a mixture of water and other constituents. The aqueous system may contain oil. The aqueous system may comprise an oil and water emulsion. The aqueous system may comprise solids. The aqueous system may comprise suspended solids. The aqueous system may comprise high levels of dissolved solids. The aqueous system may comprise one or more salts, for example sodium chloride. Suitably, the aqueous system consists of a body of water. Suitably, the aqueous system consists of a body of water which comprises water and other constituents, for example dissolved solids.

Suitably, the aqueous system comprises an industrial water system. The aqueous system may consist of industrial water. The aqueous system may consist of industrial water which may comprise water and other constituents. The aqueous system may comprise a cooling water system. The aqueous system may consist of cooling water which may comprise water and other constituents. The aqueous system may comprise a pulping and papermaking system. The aqueous system may consist of pulping and papermaking water which may comprise water and other constituents. The aqueous system may comprise an oil and gas field water system. The aqueous system may consist of oil and gas field water which may comprise water and other constituents. The aqueous system may comprise a well treatment fluid. The aqueous system may consist of well treatment fluid which may comprise water and other constituents.

Suitably, the method comprises treating industrial water to inhibit growth of one or more micro-organisms therein and/or to reduce the number of live micro-organisms therein, wherein the method comprises adding treatment agents to said industrial water. The method may comprise treating cooling water to inhibit growth of one or more micro-organisms therein and/or to reduce the number of live micro-organisms therein, wherein the method comprises adding treatment agents to said cooling water. The method may comprise treating pulping and papermaking water to inhibit growth of one or more micro-organisms therein and/or to reduce the number of live micro-organisms therein, wherein the method comprises adding treatment agents to said pulping and papermaking water. The method may comprise treating oil and gas field water to inhibit growth of one or more micro-organisms therein and/or to reduce the number of live micro-organisms therein, wherein the method comprises adding treatment agents to said oil and gas field water. The method may comprise treating a well treatment fluid to inhibit growth of one or more micro-organisms therein and/or to reduce the number of live micro-organisms therein, wherein the method comprises adding treatment agents to well treatment fluid.

Suitably, the method comprises treating an aqueous system which comprises dissolved solids.

Suitably, the method comprises treating an aqueous system having a total dissolved solids (TDS) of 1000 mg $l^{-1}$ or greater. Suitably, the aqueous system has a total dissolved solids (TDS) of at least 2000 mg $l^{-1}$, for example at least: 3000 mg $l^{-1}$; 4000 mg $l^{-1}$; 5000 mg $l^{-1}$; 6000 mg $l^{-1}$; 7000 mg $l^{-1}$; 8000 mg $l^{-1}$; or 9000 mg $l^{-1}$.

Suitably, the method comprises treating an aqueous system having a total dissolved solids (TDS) of 10,000 mg $l^{-1}$ or greater. Suitably, the aqueous system has a total dissolved solids (TDS) of at least 11,000 mg $l^{-1}$, for example at least: 12,000 mg $l^{-1}$; 13,000 mg $l^{-1}$; 14,000 mg $l^{31\ 1}$; 15,000 mg $l^{-1}$; 16,000 mg $l^{-1}$; 17,000 mg $l^{-1}$; 18,000 mg $l^{-1}$; or 19,000 mg $l^{-1}$.

Suitably, the method comprises treating an aqueous system having a total dissolved solids (TDS) of 20,000 mg $l^{-1}$ or greater. Suitably, the aqueous system has a total dissolved solids (TDS) of at least 21,000 mg $l^{-1}$, for example at least: 22,000 mg $l^{-1}$; 23,000 mg $l^{-1}$; 24,000 mg $l^{-1}$; 25,000 mg $l^{-1}$; 26,000 mg $l^{-1}$; 27,000 mg $l^{-1}$; 28,000 mg $l^{-1}$; or 29,000 mg $l^{-1}$.

Suitably, the method comprises treating an aqueous system having a total dissolved solids (TDS) of 30,000 mg $l^{-1}$ or greater. Suitably, the aqueous system has a total dissolved solids (TDS) of at least 31,000 mg $l^{-1}$, for example at least: 32,000 mg $l^{-1}$; for example at least: 33,000 mg $l^{-1}$; 34,000 mg $l^{-1}$; 35,000 mg $l^{-1}$; 36,000 mg $l^{-1}$; 37,000 mg $l^{-1}$; 38,000 mg $l^{-1}$; 39,000 mg $l^{-1}$; or 40,000 mg $l^{-1}$.

The method may comprise treating an aqueous system having a total dissolved solids (TDS) of 50,000 mg $l^{-1}$ or greater. The aqueous system may have a total dissolved solids (TDS) of at least 60,000 mg $l^{-1}$, for example at least: 70,000 mg $l^{-1}$; 80,000 mg $l^{-1}$; 90,000 mg $l^{-1}$; 100,000 mg $l^{-1}$; 110,000 mg $l^{-1}$; 120,000 mg $l^{-1}$; 130,000 mg $l^{-1}$; 140,000 mg $l^{-1}$; 150,000 mg $l^{-1}$; 160,000 mg $l^{-1}$; 170,000 mg $l^{-1}$; 180,000 mg $l^{-1}$; 190,000 mg $l^{-1}$; 200,000 mg $l^{-1}$; 210,000 mg $l^{-1}$; 220,000 mg $l^{-1}$; 230,000 mg $l^{-1}$; 240,000 mg $l^{-1}$; or 250,000 mg $l^{-1}$; 260,000 mg $l^{-1}$; 270,000 mg $l^{-1}$; 280,000 mg $l^{-1}$; 290,000 mg $l^{-1}$; 300,000 mg $l^{-1}$.

Suitably, the method comprises treating an aqueous system having a total dissolved solids (TDS) of 250,000 mg $l^{-1}$ or less. The aqueous system may have a total dissolved solids (TDS) of no more than 240,000 mg $l^{-1}$, for example no more than 230,000 mg $l^{-1}$; 220,000 mg $l^{-1}$; 210,000 mg $l^{-1}$; 200,000 mg $l^{-1}$; 190,000 mg $l^{-1}$; 180,000 mg $l^{-1}$; 170,000 mg $l^{-1}$; 160,000 mg $l^{-1}$; 150,000 mg $l^{-1}$; 140,000 mg $l^{-1}$; 130,000 mg $l^{-1}$; 120,000 mg $l^{-1}$; or 110,000 mg $l^{-1}$.

Suitably, the method comprises treating an aqueous system having a total dissolved solids (TDS) of 100,000 mg $l^{-1}$ or less. The aqueous system may have a total dissolved solids (TDS) of no more than 90,000 mg $l^{-1}$, for example no more than 80,000 mg $l^{-1}$; 70,000 mg $l^{-1}$; 60,000 mg $l^{-1}$; 50,000 mg $l^{-1}$; or 40,000 mg $l^{-1}$.

Suitably, the method comprises treating an aqueous system having a total dissolved solids (TDS) of at least 25,000 mg $l^{-1}$. Suitably, the method comprises treating an aqueous system having a total dissolved solids (TDS) of at least 30,000 mg $l^{-1}$.

Suitably, the method comprises treating an aqueous system having a total dissolved solids (TDS) of from 10,000 mg $l^{-1}$ to 300,000 mg $l^{-1}$. Suitably, the method comprises treating an aqueous system having a total dissolved solids (TDS) of from 10,000 mg $l^{-1}$ to 100,000 mg $l^{-1}$. Suitably, the aqueous system has a total dissolved solids (TDS) of from 20,000 mg $l^{-1}$ to 100,000 mg $l^{-1}$, for example from 25,000 mg $l^{-1}$ to 100,000 mg $l^{-1}$. Suitably, the aqueous system has a total dissolved solids (TDS) of from 30,000 mg $l^{-1}$ to 100,000 mg $l^{-1}$. Suitably, the method comprises treating an aqueous system having a total dissolved solids (TDS) of from 20,000 mg $l^{-1}$ to 80,000 mg $l^{-1}$, for example from 25,000 mg $l^{-1}$ to 80,000 mg $l^{-1}$. Suitably, the method comprises treating an aqueous system having a total dissolved solids (TDS) of from 30,000 mg $l^{-1}$ to 80,000 mg $l^{-1}$.

Suitably, the method comprises treating an aqueous system to inhibit the growth of a plurality of different micro-organisms.

Suitably, the method comprises treating an aqueous system to prevent the growth of one or more micro-organisms. Suitably, the method comprises treating an aqueous system to prevent the growth of a plurality of different micro-organisms.

Suitably, the method comprises treating an aqueous system to kill one or more micro-organisms. Suitably, the method comprises treating an aqueous system to kill a plurality of different micro-organisms.

Suitably, the method comprises treating an aqueous system to inhibit or prevent the growth of one or more micro-organisms therein and/or to reduce the number of live micro-organisms therein, wherein said micro-organisms are selected from bacteria, fungi and algae. Suitably, the method comprises a method of inhibiting growth of bacteria and/or killing bacteria. Suitably, the method comprises a method of inhibiting growth of fungi and/or killing fungi. Suitably, the method comprises a method of inhibiting growth of algae and/or killing algae.

Suitably, the method comprises treating an aqueous system to inhibit or prevent the growth of anaerobic micro-organisms. Suitably, the method comprises treating an aqueous system to kill anaerobic micro-organisms. Suitably, the method comprises treating an aqueous system to inhibit or prevent the growth of anaerobic bacteria. Suitably, the method comprises treating an aqueous system to kill anaerobic bacteria. Suitably, the method comprises treating an aqueous system to inhibit or prevent the growth of facultative anaerobic bacteria. Suitably, the method comprises treating an aqueous system to kill facultative anaerobic bacteria.

Suitably, the method comprises treating an aqueous system to inhibit or prevent the growth of aerobic micro-organisms. Suitably, the method comprises treating an aqueous system to kill aerobic micro-organisms. Suitably, the method comprises treating an aqueous system to inhibit or prevent the growth of aerobic bacteria. Suitably, the method comprises treating an aqueous system to kill aerobic bacteria.

Suitably, the method comprises treating an aqueous system to inhibit or prevent the growth of anaerobic and aerobic micro-organisms. Suitably, the method comprises treating an aqueous system to kill anaerobic and aerobic micro-organisms. Suitably, the method comprises treating an aqueous system to inhibit or prevent the growth of anaerobic and aerobic bacteria. Suitably, the method comprises treating an aqueous system to kill anaerobic and aerobic bacteria.

The method may comprise a method of inhibiting growth of gram-positive aerobic bacteria, gram-positive facultative anaerobic bacteria, gram-negative aerobic bacteria, gram-negative facultative anaerobic bacteria, gram-positive anaerobic bacteria and/or gram-negative anaerobic bacteria. The method may comprise a method of inhibiting growth of mold and/or yeast. The method may comprise a method of inhibiting the growth of blue green algae and/or green algae. Suitably, the method comprises a method of inhibiting the growth of gram-negative aerobic bacteria, gram-negative facultative anaerobic bacteria, gram-negative anaerobic bacteria, and green algae. Suitably, the method comprises inhibiting the growth of *Pseudomonas aeruginosa* bacteria in an aqueous system. Suitably, the method comprises inhibiting the growth of *Enterobacter aerogenes* bacteria in an aqueous system. Suitably, the method comprises inhibiting the growth of *Desulfovibrio vulgaris* bacteria in an aqueous system. Suitably, the method comprises inhibiting the growth of *Chlorella vulgaris* algae in an aqueous system.

Suitably, the method comprises adding a phosphonium compound treatment agent and an oxazolidine compound treatment agent to an aqueous system such that a Log 10 reduction of 1 or greater in an anaerobe culture is obtained after a contact time of 24 hours. Suitably, the method comprises obtaining a Log 10 reduction of 2 or greater to an anaerobe culture after a contact time of 24 hours; for example of 3 or greater; 4 or greater; or 5 or greater.

Suitably, the method comprises adding a phosphonium compound and an oxazolidine compound to an aqueous system such that a complete kill of an anaerobe culture is obtained after a contact time of 24 hours.

Suitably, the method comprises adding a phosphonium compound treatment agent and an oxazolidine compound treatment agent to an aqueous system such that a Log 10 reduction of 1 or greater in an anaerobe culture is obtained after a contact time of 4 hours. Suitably, the method comprises obtaining a Log 10 reduction of 2 or greater to an anaerobe culture after a contact time of 4 hours; for example of 3 or greater; 4 or greater; or 5 or greater.

Suitably, the method comprises adding a phosphonium compound and an oxazolidine compound to an aqueous system such that a complete kill of an anaerobe culture is obtained after a contact time of 4 hours.

Suitably, the method comprises adding a phosphonium compound treatment agent and an oxazolidine compound treatment agent to an aqueous system such that a Log 10 reduction of 1 or greater in an anaerobe culture is obtained after a contact time of 1 hour. Suitably, the method comprises obtaining a Log 10 reduction of 2 or greater to an anaerobe culture after a contact time of 1 hours; for example of 3 or greater; 4 or greater; or 5 or greater.

Suitably, the method comprises adding a phosphonium compound and an oxazolidine compound to an aqueous system such that a complete kill of an anaerobe culture is obtained after a contact time of 1 hour.

Suitably, the method comprises adding a phosphonium compound treatment agent and a oxazolidine compound treatment agent to an aqueous system such that a Log 10 reduction of 1 or greater in a facultative anaerobe culture is obtained after a contact time of 24 hours. Suitably, the method comprises obtaining a Log 10 reduction of 2 or greater to a facultative anaerobe culture after a contact time of 24 hours; for example of 3 or greater; 4 or greater; or 5 or greater. Suitably, the method comprises obtaining a Log 10 reduction of 6 or greater to a facultative anaerobe culture after a contact time of 24 hours; for example of 7 or greater; or 8 or greater.

Suitably, the method comprises adding a phosphonium compound, and an oxazolidine compound to an aqueous system such that a complete kill of a facultative anaerobe culture is obtained after a contact time of 24 hours.

Suitably, the method comprises adding a phosphonium compound treatment agent and a oxazolidine compound treatment agent to an aqueous system such that a Log 10 reduction of 1 or greater in a facultative anaerobe culture is obtained after a contact time of 4 hours. Suitably, the method comprises obtaining a Log 10 reduction of 2 or greater to a facultative anaerobe culture after a contact time of 4 hours; for example of 3 or greater; 4 or greater; 5 or greater; or 6 or greater.

Suitably, the method comprises adding a phosphonium compound treatment agent and a oxazolidine compound treatment agent to an aqueous system such that a Log 10 reduction of 1 or greater in a facultative anaerobe culture is obtained after a contact time of 1 hour. Suitably, the method comprises obtaining a Log 10 reduction of 2 or greater to a facultative anaerobe culture after a contact time of 1 hours; for example of 3 or greater; or 4 or greater.

The method may comprise adding a phosphonium compound treatment agent and a oxazolidine compound treatment agent to an aqueous system such that a Log 10 reduction of 1 or greater in an aerobe culture is obtained after a contact time of 24 hours. The method may comprise obtaining a Log 10 reduction of 2 or greater to an aerobe culture after a contact time of 24 hours; for example of 3 or greater; 4 or greater; 5 or greater; or 6 or greater.

The method may comprise adding a phosphonium compound treatment agent and a oxazolidine compound treatment agent to an aqueous system such that a Log 10 reduction of 1 or greater in an aerobe culture is obtained after a contact time of 4 hours. The method may comprise obtaining a Log 10 reduction of 2 or greater to an aerobe culture after a contact time of 4 hours; for example of 3 or greater; 4 or greater; 5 or greater; or 6 or greater.

The method may comprise adding a phosphonium compound treatment agent and a oxazolidine compound treatment agent to an aqueous system such that a Log 10 reduction of 1 or greater in an aerobe culture is obtained after a contact time of 1 hour. The method may comprise obtaining a Log 10 reduction of 2 or greater to an aerobe culture after a contact time of 1 hours; for example of 3 or greater; or 4 or greater.

Suitably, the method comprises adding treatment agents to an aqueous system such that compound (a) and compound (b) are added to the aqueous system in a total amount of from 1 to 1000 parts by weight active per one million parts by weight of said aqueous system (ppm), for example from 5 to 800 ppm.

As used herein, all references to ppm refer to parts per million by weight unless stated otherwise.

Suitably, the method comprises adding compound (a) and compound (b) to the aqueous system such that they are added in a total amount of from 5 to 600 ppm. Suitably, the method comprises adding compound (a) and compound (b) to the aqueous system such that they are added in a total amount of from 5 to 500 ppm. Suitably, the method comprises adding compound (a) and compound (b) to the aqueous system such that they are added in a total amount of from 10 to 400 ppm, for example 10 to 300 ppm. Suitably, the method comprises adding compound (a) and compound (b) to the aqueous system such that they are added in a total amount of from 10 to 200 ppm, for example 20 to 200 ppm. Suitably, the method comprises adding compound (a) and compound (b) to the aqueous system such that they are added in a total amount of from 30 to 200 ppm, for example 40 to 150 ppm.

Suitably, the method comprises adding a oxazolidine compound treatment agent to an aqueous system in an amount of at least 5 parts per million (ppm).

Suitably, the method comprises adding a oxazolidine compound treatment agent to an aqueous system to provide a treated aqueous system comprising said oxazolidine compound in an amount of at least 1 part per million (ppm).

The method may comprise adding an aqueous solution comprising an oxazolidine compound to an aqueous system. The method may comprise adding an aqueous solution comprising 4,4-dimethyloxazolidine to an aqueous system.

The method may comprise adding an oxazolidine composition to an aqueous system.

Suitably, the method comprises adding an oxazolidine compound to an aqueous system such that it is added in an amount of greater than 5 ppm. Suitably, the method comprises adding an oxazolidine compound to an aqueous system such that it is added in an amount of at least 10 ppm. Suitably, the method comprises adding an oxazolidine compound to an aqueous system such that it is added in an amount of at least: 15 ppm, for example at least: 20 ppm; 25 ppm; 30 ppm; 35 ppm or 40 ppm. The method may comprise adding an oxazolidine compound to an aqueous system such that it is added in an amount of at least 50 ppm, for example at least: 60 ppm; 70 ppm; 80 ppm; 90 ppm or 100 ppm.

Suitably, the method comprises adding an oxazolidine compound to an aqueous system such that it is present in an active amount of greater than 1 ppm. Suitably, the method comprises adding an oxazolidine compound to an aqueous system such that it is present in an active amount of at least 5 ppm. Suitably, the method comprises adding an oxazolidine compound to an aqueous system such that it is present in an active amount of at least 10 ppm, for example at least: 15 ppm; 20 ppm; 25 ppm; 30 ppm; 35 ppm or 40 ppm. The method may comprise adding an oxazolidine compound to an aqueous system such that it is present in an active amount of at least 60 ppm; 70 ppm; 80 ppm; 90 ppm or 100 ppm.

Suitably, the method comprises adding an oxazolidine compound to an aqueous system such that it is added in an amount of not more than 800 ppm. Suitably, the method comprises adding an oxazolidine compound to an aqueous system such that it is added in an amount of not more than 700 ppm; for example not more than: 600 ppm; or 500 ppm. Suitably, the method comprises adding an oxazolidine compound to an aqueous system such that it is added in an amount of not more than 400 ppm.

Suitably, the method comprises adding an oxazolidine compound to an aqueous system such that it is present in an active amount of not more than 500 ppm. Suitably, the method comprises adding an oxazolidine compound to an aqueous system such that it is present in an active amount of not more than 400 ppm, for example not more than 300 ppm. Suitably, the method comprises adding an oxazolidine compound to an aqueous system such that it is present in an active amount of not more than 200 ppm, for example not more than 100 ppm.

Suitably, the method comprises adding an oxazolidine compound to an aqueous system to provide a treated aqueous system comprising said oxazolidine compound in an amount of 1 to 500 ppm, for example 10 to 400 ppm. The method may comprise adding an oxazolidine compound to an aqueous system to provide a treated aqueous system comprising said oxazolidine compound in an amount of 20 to 100 ppm, for example 30 to 90 ppm.

Suitably, the method comprises adding 4,4-dimethyloxazolidine to an aqueous system such that it is added in an amount of at least 5 ppm. Suitably, the method comprises adding 4,4-dimethyloxazolidine to an aqueous system such that it is added in an amount of at least 10 ppm. Suitably, the method comprises adding 4,4-dimethyloxazolidine to an aqueous system such that it is added in an amount of at least: 15 ppm, for example at least: 20 ppm; 25 ppm; 30 ppm; 35 ppm or 40 ppm. The method may comprise adding 4,4-dimethyloxazolidine to an aqueous system such that it is added in an amount of at least 50 ppm, for example at least: 60 ppm; 70 ppm; 80 ppm; 90 ppm or 100 ppm.

Suitably, the method comprises adding 4,4-dimethyloxazolidine to an aqueous system such that it is present in an active amount of at least 1 ppm. Suitably, the method comprises adding 4,4-dimethyloxazolidine to an aqueous system such that it is present in an active amount of at least 5 ppm. Suitably, the method comprises adding 4,4-dimethyloxazolidine to an aqueous system such that it is present in an active amount of at least 10 ppm, for example at least: 15 ppm; 20 ppm; 25 ppm; 30 ppm; 35 ppm or 40 ppm. The method may comprise adding 4,4-dimethyloxazolidine to an aqueous system such that it is present in an active amount of at least 60 ppm; 70 ppm; 80 ppm; 90 ppm or 100 ppm.

Suitably, the method comprises adding 4,4-dimethyloxazolidine to an aqueous system such that it is added in an amount of not more than 800 ppm. Suitably, the method comprises adding 4,4-dimethyloxazolidine to an aqueous system such that it is added in an amount of not more than 700 ppm; for example not more than: 600 ppm; or 500 ppm. Suitably, the method comprises adding 4,4-dimethyloxazolidine to an aqueous system such that it is added in an amount of not more than 400 ppm.

Suitably, the method comprises adding 4,4-dimethyloxazolidine to an aqueous system such that it is present in an active residual amount of not more than 500 ppm. Suitably, the method comprises adding 4,4-dimethyloxazolidine to an aqueous system such that it is present in an active residual amount of not more than 400 ppm, for example not more than 300 ppm. Suitably, the method comprises adding 4,4-dimethyloxazolidine to an aqueous system such that it is present in an active residual amount of not more than 200 ppm, for example not more than 100 ppm.

Suitably, the method comprises adding 4,4-dimethyloxazolidine to an aqueous system to provide a treated aqueous system comprising 4,4-dimethyloxazolidine in an amount of 1 to 500 ppm, for example 10 to 400 ppm. The method may comprise adding 4,4-dimethyloxazolidine to an aqueous system to provide a treated aqueous system comprising 4,4-dimethyloxazolidine in an amount of 20 to 100 ppm, for example 30 to 90 ppm.

Suitably, the method comprises adding a phosphonium compound treatment agent to an aqueous system in an amount of at least 0.1 parts per million (ppm).

Suitably, the method comprises adding a phosphonium compound treatment agent to an aqueous system to provide a treated aqueous system comprising said phosphonium compound in an amount of at least 0.1 parts per million (ppm).

Suitably, the method comprises adding a phosphonium compound to an aqueous system such that it is added in an amount of at least 0.2 ppm. Suitably, the method comprises adding a phosphonium compound to an aqueous system such that it is added in an amount of at least 0.3 ppm, for example at least: 0.4 ppm; 0.5 ppm; 0.6 ppm; 0.7 ppm; 0.8 ppm; 0.9 ppm; or 1.0 ppm. Suitably, the method comprises adding a phosphonium compound to an aqueous system such that it is added in an amount of at least 1 ppm; for example at least 1.5 ppm; 2.0 ppm; 2.5 ppm; 3.0 ppm; 3.5 ppm; 4.0 ppm; 4.5 ppm; 5.0 ppm; 5.5 ppm; or 6.0 ppm. The method may comprise adding a phosphonium compound to an aqueous system such that it is added in an amount of at least 6 ppm, for example at least: 7 ppm; 8 ppm; 9 ppm; 10 ppm; 11 ppm; 12 ppm.

Suitably, the method comprises adding a phosphonium compound to an aqueous system such that it is present in an active amount of at least 0.2 ppm. Suitably, the method comprises adding a phosphonium compound to an aqueous system such that it is present in an active amount of at least 0.3 ppm, for example at least: 0.4 ppm; 0.5 ppm; 0.6 ppm; 0.7 ppm; 0.8 ppm; 0.9 ppm; or 1.0 ppm. Suitably, the method comprises adding a phosphonium compound to an aqueous system such that it is present in an active amount of at least 1 ppm; for example at least 1.5 ppm; 2.0 ppm; 2.5 ppm; 3.0 ppm; 3.5 ppm; 4.0 ppm; 4.5 ppm; 5.0 ppm; 5.5 ppm; or 6.0 ppm. The method may comprise adding a phosphonium compound to an aqueous system such that it is present in an active amount of at least 6 ppm, for example at least: 7 ppm; 8 ppm; 9 ppm; 10 ppm; 11 ppm; 12 ppm.

Suitably, the method comprises adding a phosphonium compound treatment agent to an aqueous system to provide a treated aqueous system comprising said phosphonium compound added in an amount of 1 to 20 ppm, for example 1 to 15 ppm. Suitably, the method comprises adding a phosphonium compound treatment agent to an aqueous system to provide a treated aqueous system comprising said phosphonium compound added in an amount of 1 to 10 ppm, for example 2 to 8 ppm.

Suitably, the method comprises adding a phosphonium compound treatment agent to an aqueous system in an amount of not more than 250 ppm, for example not more than 125 ppm.

Suitably, the method may comprises adding a phosphonium compound treatment agent to an aqueous system in an amount of not more than 100 ppm, for example not more than 50 ppm. Suitably, the method comprises adding a phosphonium compound to an aqueous system such that it is added in an amount of not more than 40 ppm, for example not more than 35 ppm. The method may comprise adding a phosphonium compound to an aqueous system such that it is added in an amount of not more than 30 ppm, for example not more than; 25 ppm; 20 ppm; 15 ppm; 10 ppm or 5 ppm.

Suitably, the method comprises adding a phosphonium compound treatment agent to an aqueous system to provide a treated aqueous system comprising said phosphonium compound in an active amount of not more than 250 ppm, for example not more than 125 ppm.

Suitably, the method comprises adding a phosphonium compound treatment agent to an aqueous system to provide a treated aqueous system comprising said phosphonium compound in an active amount of not more than 100 ppm, for example not more than 50 ppm. Suitably, the method comprises adding a phosphonium compound to an aqueous system such that it is present in an active amount of not more than 40 ppm, for example not more than 35 ppm. The method may comprise adding a phosphonium compound to an aqueous system such that it is present in an amount of not more than 30 ppm, for example not more than; 25 ppm; 20 ppm; 15 ppm; 10 ppm; or 5 ppm.

Suitably, the method comprises adding a phosphonium compound (a) and a oxazolidine compound (b) to an aqueous system in a weight ratio, expressed as active compound, of phosphonium compound:oxazolidine compound of from 1.0:0.5 to 1.0:100.0, for example from 1.0:1.0 to 1.0:50.0.

As used herein, all ratios are weight ratios unless stated otherwise.

Suitably, the method comprises adding a phosphonium compound (a) and a oxazolidine compound (b) to an aqueous system in a weight ratio, expressed as active compound, of phosphonium compound:oxazolidine compound of from 1.0:2.0 to 1.0:20.0, for example from 1.0:3.0 to 1.0:15.0.

Suitably, the method comprises adding a phosphonium compound (a) and a oxazolidine compound (b) to an aqueous system in a weight ratio, expressed as active compound, of phosphonium compound:oxazolidine compound of from 1.0:1.0 to 1.0:10.0, for example from 1.0:5.0 to 1.0:8.0.

Suitably, the method comprises adding a phosphonium compound (a) and a oxazolidine compound (b) to an aqueous system in a weight ratio, expressed as active compound, of phosphonium compound:oxazolidine compound of from 1.0:5.0 to 1.0:20.0, for example from 1.0:11.0 to 1.0:15.0.

The method may comprise adding a phosphonium compound (a) and a oxazolidine compound (b) to an aqueous system to provide a treated aqueous system comprising said phosphonium compound (a) and said oxazolidine compound (b) in a weight ratio, expressed as active compound, of phosphonium compound:oxazolidine containing compound of at least 1.0:100.0, for example at least 1.0:50.0.

Suitably the method comprises adding a phosphonium compound (a) and a oxazolidine compound (b) to an aqueous system to provide a treated aqueous system comprising said phosphonium compound (a) and said oxazolidine compound (b) in a weight ratio, expressed as active compound, of phosphonium compound:oxazolidine compound of at least 1.0:20.0, for example of at least: 1.0:15.0.

Suitably the method comprises adding a phosphonium compound (a) and a oxazolidine compound (b) to an aqueous system to provide a treated aqueous system comprising said phosphonium compound (a) and said oxazolidine compound (b) in a weight ratio, expressed as active compound, of phosphonium compound:oxazolidine containing compound of no greater than 1.0:0.5, for example no greater than 1.0:1.0.

The method may comprise adding a phosphonium compound (a) and a oxazolidine compound (b) to an aqueous system to provide a treated aqueous system comprising said phosphonium compound (a) and said oxazolidine compound (b) in a weight ratio, expressed as active compound, of phosphonium compound:oxazolidine containing compound of no greater than 1.0:2.0, for example no greater than 1.0:5.0.

The method may comprise adding a combination of phosphonium compounds (a) to an aqueous system. Suitably, the method comprises adding a single type of phosphonium compound (a) to an aqueous system.

Suitably, the method employs a phosphonium compound (a) having formula:

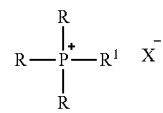

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}$-$C_{16}$ alkyl group. Suitably, $R^1$ is a tetradecyl group.

Suitably, X is chlorine.

Suitably, the method employs a phosphonium compound (a) which is a phosphonium chloride.

Suitably, the method comprises treating an aqueous system such that phosphonium chloride comprises greater than 50% of the total phosphonium compound(s) added to the aqueous system. Suitably, the method comprises treating an aqueous system such that phosphonium chloride comprises greater than 90% of the total phosphonium compound(s) added to the aqueous system, for example 99% or greater.

Suitably, the method comprises treating an aqueous system such that phosphonium chloride comprises greater than 50% of the total phosphonium compound(s) present in the aqueous system. Suitably, the method comprises treating an aqueous system such that phosphonium chloride comprises greater than 90% of the total phosphonium compound(s) present in the aqueous system, for example 99% or greater.

Suitably, the method employs a phosphonium chloride as the only phosphonium compound (a).

Suitably, the method comprises adding tri n-butyl n-tetradecyl phosphonium chloride (hereafter "TTPC") to the aqueous system. Suitably, the phosphonium compound (a) comprises TTPC. Suitably, the phosphonium compound (a) consists of TTPC.

Suitably, the method comprises adding an aqueous composition containing the phosphonium compound (a) to the aqueous system. Suitably, the method comprises adding an aqueous composition of TTPC to the aqueous system. The method may comprise adding an aqueous composition comprising 5% by weight of TTPC to the aqueous system. A suitable composition containing TTPC is available from BWA Water Additives and is sold under the trade name Bellacide 355 (an aqueous composition of TTPC and water consisting of water and 5% by weight of TTPC). The method may comprise adding an aqueous composition comprising 50% by weight of TTPC to the aqueous system. A suitable composition containing TTPC is available from BWA Water Additives and is sold under the trade name Bellacide 350 (an aqueous composition of TTPC and water consisting of water and 50% by weight of TTPC).

Suitably, the method comprises treating an aqueous system such that TTPC comprises greater than 50% of the total phosphonium compound(s) added to the aqueous system.

Suitably, the method comprises treating an aqueous system such that TTPC comprises greater than 90% of the total phosphonium compound(s) added to the aqueous system, for example 99% or greater.

Suitably, the method comprises treating an aqueous system such that TTPC comprises greater than 50% of the total phosphonium compound(s) present in the aqueous system. Suitably, the method comprises treating an aqueous system such that TTPC comprises greater than 90% of the total phosphonium compound(s) present in the aqueous system, for example 99% or greater.

Suitably, the method employs TTPC as the only phosphonium compound (a).

The method may employ a synergistic mixture of compound (a) and compound (b). Suitably, by "synergistic mixture" it is meant that the mixture of compounds (a) and compound (b) has a synergistic effect on the inhibition of growth of one or more biological organisms, preferably micro-organisms such as bacteria, fungi and/or algae and/or has a synergistic effect on reducing the number of one or more biological organisms, preferably micro-organisms such as bacteria, fungi and/or algae.

The method may comprise adding compound (a) and compound (b) to the aqueous system such that the aqueous system comprises a synergistic mixture of compound (a) and compound (b).

The method may comprise adding compound (a) and compound (b) as a mixture to the aqueous system. The method may comprise adding compound (a) and compound (b) separately to the aqueous system and allowing or causing them to mix within the aqueous system.

Where the method comprises mixing compound (a) and compound (b) and adding the mixture to the aqueous system and/or adding compound (a) and compound (b) separately to the aqueous system and allowing or causing them to mix within the aqueous system then compound (a) and compound (b) are suitably used in the form of aqueous compositions.

Suitably, compound (a) is used in the form of an aqueous composition comprising between 1% and 90% by weight of compound (a), for example between 1% and 60% by weight. Suitably, compound (a) is used in the form of an aqueous composition comprising between 1% and 10% by weight of compound (a), for example 5% by weight.

Suitably, compound (b) is used in the form of an aqueous composition comprising between 10% and 90% by weight of compound (b), for example between 50% and 80%. Suitably, compound (b) is used in the form of an aqueous composition comprising between 70% and 80% by weight of compound (b), for example between 70% and 75%.

The method may comprise a method of treating an industrial water system. The method may comprise treating a cooling water system. The method may comprise treating a pulping and/or papermaking water system. The method may comprise treating an oil and/or gas field water system. The method may comprise treating an aqueous system to control the growth of bacterial and/or algal micro-organisms contained therein and/or which may become entrained in said system.

It has been found that the compositions and methods of utilisation of the present invention may in particular be efficacious in controlling acid producing facultative anaerobic bacteria and hydrogen sulphide producing anaerobic bacteria which may populate aqueous systems.

Surprisingly, it has been found that when compound (a) and compound (b) are combined the resulting combination may pose a higher degree of biocidal activity in an aqueous system than that of the individual compounds used alone. Because of the enhanced activity of the combination of treatment agent compounds, it may be possible for the total quantity of treatment agent added to an aqueous system to be reduced in comparison to a system using only one of said treatment agent compounds. In addition, the high degree of biocidal activity which is provided by each of the treatment agent compounds may be exploited without use of higher concentrations of each. The combination of TTPC and 4,4-dimethyloxazolidine may be particularly effective. The composition may also be surprisingly effective in systems having high total dissolved solids (TDS).

It has been found that the compositions and methods of utilisation of the present invention may in particular be efficacious in controlling the facultative anaerobic bacterium *Enterobacter aerogenes* and/or the anaerobic bacterium *Desulfovibrio vulgaris*, which may populate aqueous systems.

Surprisingly, the present inventor has found that mixtures of compound (a) and compound (b) such as mixtures of tri-n-butyl n-tetradecyl phosphonium chloride (TTPC) and 4,4-dimethyloxazolidine are especially efficacious in controlling the growth of micro-organisms such as bacterial and algal microbes in aqueous systems comprising dissolved solids and there is an unexpected synergistic relationship.

It has been found that compositions of compounds (a) and compound (b) may be unexpectedly effective against facultative anaerobes and anaerobes and may have a marked synergy in relation to anaerobes at short contact times. For example, 4,4-dimethyloxazolidine may have some biocidal activity against anaerobes at short contact times but the addition of TTPC may greatly improve performance even though TTPC alone may be ineffective against anaerobes at short contact times According to a second aspect of the present invention there is provided a method of treating an aqueous system to inhibit growth of one or more micro-organisms therein and/or to reduce the number of live micro-organisms therein, wherein the method comprises adding treatment agents to said aqueous system and wherein said treatment agents comprise:
(i) tri n-butyl n-tetradecyl phosphonium chloride (TTPC); and
(ii) 4,4-dimethyloxazolidine (DMO).

Suitably, the aqueous system comprises dissolved solids.
Suitably, the aqueous system comprises greater than 10,000 mg $l^{-1}$ total dissolved solids (TDS). The aqueous system may comprise greater than 20,000 mg $l^{-1}$ TDS, for example greater than 30,000 mg $l^{-1}$ TDS.

The method of the second aspect may comprise any feature as described in relation to the first aspect except where such features are mutually exclusive.

According to a third aspect of the present invention there is provided an aqueous system comprising a combination of:
(a) a phosphonium compound; and
(b) an oxazolidine compound.

Suitably, the aqueous system comprises dissolved solids.
Suitably, the aqueous system comprises greater than 10,000 mg $l^{-1}$ total dissolved solids (TDS). The aqueous system may comprise greater than 20,000 mg $l^{-1}$ TDS, for example greater than 30,000 mg $l^{-1}$ TDS.

Suitably, the phosphonium compound (a) has formula:

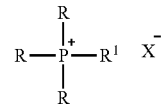

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}$-$C_{16}$ alkyl group. Suitably, $R^1$ is a tetradecyl group.

Suitably, X is chlorine.

Suitably, the phosphonium compound (a) is a phosphonium chloride.

Suitably, said compound (a) comprises TTPC.

Suitably, the oxazolidine compound (b) comprise a methyloxazolidine. Suitably, the oxazolidine compound (b) comprise a dimethyloxazolidine.

Suitably, said compound (b) comprises 4,4-dimethyloxazolidine.

Suitably the aqueous system comprises a mixture of water and other constituents. The aqueous system may contain oil. The aqueous system may comprise an oil and water emulsion. The aqueous system may comprise solids. The aqueous system may comprise suspended solids. The aqueous system may comprise high levels of dissolved solids. The aqueous system may comprise one or more salts, for example sodium chloride. Suitably, the aqueous system consists of a body of water. Suitably, the aqueous system consists of a body of water which comprises water and other constituents, for example dissolved solids.

Suitably, the aqueous system comprises an industrial water system. The aqueous system may consist of industrial water. The aqueous system may comprise a cooling water system. The aqueous system may comprise a pulping and papermaking system. The aqueous system may comprise an oil and gas field water system. The aqueous system may comprise a well treatment fluid.

The aqueous system may comprise cooling water. The aqueous system may consist of cooling water, comprising compound (a), compound (b) and optionally other constituents in addition to water. The aqueous system may comprise pulping and papermaking water. The aqueous system may consist of pulping and papermaking water, comprising compound (a), compound (b) and optionally other constituents in addition to water. The aqueous system may comprise oil and gas field water. The aqueous system may consist of oil and gas field water, comprising compound (a), compound (b) and optionally other constituents in addition to water. The aqueous system may comprise well treatment fluid. The aqueous system may consist of well treatment fluid, comprising compound (a), compound (b) and optionally other constituents in addition to water.

The aqueous system of the third aspect may comprise any feature as described in relation to one or more of the first and/or second aspects except where such features are mutually exclusive.

According to a fourth aspect of the present invention there is provided a method of inhibiting or preventing the growth of one or more micro-organisms in a water based liquid, wherein the method comprises adding treatment agents to said water based liquid and wherein said treatment agents comprise:

(a) a phosphonium compound; and
(b) a oxazolidine compound.

The water based liquid may consist of water. Suitably, the water based liquid comprises water and other constituents.

Suitably, the water based liquid comprises dissolved solids.

Suitably, the water based liquid is an aqueous media comprising water and other constituents. Suitably, the water based liquid is an aqueous media comprising water and dissolved solids.

Suitably, there is provided a method of inhibiting or preventing the growth of one or more micro-organisms in an aqueous media, wherein the method comprises adding treatment agents to an aqueous media comprising dissolved solids and wherein said treatment agents comprise:

(a) a phosphonium compound; and
(b) a oxazolidine compound.

Suitably, the water based liquid comprises greater than 10,000 mg l$^{-1}$ total dissolved solids (TDS). The aqueous system may comprise greater than 20,000 mg l$^{-1}$ TDS, for example greater than 30,000 mg l$^{-1}$ TDS.

Suitably, the phosphonium compound (a) has formula:

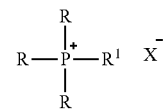

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}$-$C_{16}$ alkyl group. Suitably, $R^1$ is a tetradecyl group.

Suitably, X is chlorine.

Suitably, the phosphonium compound (a) is a phosphonium chloride.

Suitably, said compound (a) comprises TTPC.

Suitably, the oxazolidine compound (b) comprise a methyloxazolidine. Suitably, the oxazolidine compound (b) comprise a dimethyloxazolidine.

Suitably, said compound (b) comprises 4,4-dimethyloxazolidine.

Suitably the water based liquid comprises a mixture of water and other constituents. The water based liquid may contain oil. The water based liquid may comprise an oil and water emulsion. The water based liquid may comprise solids. The water based liquid may comprise suspended solids. The water based liquid may comprise high levels of dissolved solids. The water based liquid may comprise one or more salts, for example sodium chloride.

The water based liquid may comprise industrial water. The water based liquid may consist of industrial water which may comprise water and other constituents. The water based liquid may comprise cooling water. The water based liquid may consist of cooling water which may comprise water and other constituents. The water based liquid may comprise pulping and papermaking water. The water based liquid may consist of pulping and papermaking water which may comprise water and other constituents. The water based liquid may comprise oil and gas field water. The water based liquid may consist of oil and gas field water which may comprise water and other constituents. The water based liquid may comprise a well treatment fluid. The water based liquid may consist of well treatment fluid which may comprise water and other constituents.

Suitably, the method comprises treating industrial water to inhibit growth of one or more micro-organisms therein and/or to reduce the number of live micro-organisms therein. The method may comprise treating cooling water to inhibit growth of one or more micro-organisms therein and/or to reduce the number of live micro-organisms therein. The method may comprise treating pulping and papermaking water to inhibit growth of one or more micro-organisms therein and/or to reduce the number of live micro-organisms therein. The method may comprise treating oil and gas field water to inhibit growth of one or more micro-organisms therein and/or to reduce the number of live micro-organisms therein. The method may comprise treating a well treatment fluid to inhibit growth of one or more micro-organisms therein and/or to reduce the number of live micro-organisms therein.

The method of the fourth aspect may comprise any feature as described in relation to one or more of the first and/or second and/or third aspects except where such features are mutually exclusive.

According to a fifth aspect of the present invention there is provided a water based liquid comprising dissolved solids and comprising a combination of:
(a) a phosphonium compound; and
(b) an oxazolidine compound.

Suitably, the water based liquid is an aqueous media comprising water and other constituents. Suitably, the water based liquid is an aqueous media comprising water and dissolved solids.

Suitably, there is provided an aqueous media comprising dissolved solids and comprising a combination of:
(a) a phosphonium compound; and
(b) a oxazolidine compound.

Suitably, the water based liquid comprises greater than 10,000 mg l$^{-1}$ total dissolved solids (TDS). The aqueous system may comprise greater than 20,000 mg l$^{-1}$ TDS, for example greater than 30,000 mg l$^{-1}$ TDS.

Suitably, the phosphonium compound (a) has formula:

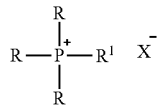

wherein each R is independently a $C_1$-$C_6$ alkyl group which is unsubstituted or substituted by a cyano, hydroxyl, esterified hydroxyl or aryl group;
$R^1$ represents a $C_8$-$C_{18}$ alkyl group which is substituted or unsubstituted; and
X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}$-$C_{16}$ alkyl group. Suitably, $R^1$ is a tetradecyl group.

Suitably, X is chlorine.

Suitably, the phosphonium compound (a) is a phosphonium chloride.

Suitably, said compound (a) comprises TTPC.

Suitably, the oxazolidine compound (b) comprise a methyloxazolidine. Suitably the oxazolidine compound (b) comprise a dimethyloxazolidine.

Suitably, said compound (b) comprises 4,4-dimethyloxazolidine.

Suitably the water based liquid comprises a mixture of water and other constituents. The water based liquid may contain oil. The water based liquid may comprise an oil and water emulsion. The water based liquid may comprise solids. The water based liquid may comprise suspended solids. The water based liquid may comprise high levels of dissolved solids. The water based liquid may comprise one or more salts, for example sodium chloride.

The water based liquid may comprise industrial water. The water based liquid may consist of industrial water, comprising compound (a), compound (b) and optionally other constituents in addition to water. The water based liquid may comprise cooling water. The water based liquid may consist of cooling water, comprising compound (a), compound (b) and optionally other constituents in addition to water. The water based liquid may comprise pulping and papermaking water. The water based liquid may consist of pulping and papermaking water, comprising compound (a), compound (b) and optionally other constituents in addition to water. The water based liquid may comprise oil and gas field water. The water based liquid may comprise oil and gas field water. The water based liquid may consist of oil and gas field water, comprising compound (a), compound (b) and optionally other constituents in addition to water. The water based liquid may comprise a well treatment fluid. The water based liquid may consist of well treatment fluid, comprising compound (a), compound (b) and optionally other constituents in addition to water.

The water based liquid of the fifth aspect may comprise any feature as described in relation to one or more of the first and/or second and/or third and/or fourth aspects except where such features are mutually exclusive.

According to a sixth aspect of the present invention there is provided a biocidal composition comprising a combination of:
(a) a phosphonium compound; and
(b) an oxazolidine compound.

Suitably, the biocidal composition comprises an aqueous composition.

The biocidal composition may comprise a combination of phosphonium compounds (a). Suitably, the biocide comprises a single type of phosphonium compound (a).

Suitably, the biocidal composition comprises one or more phosphonium compound(s), one or more oxazolidine compound(s) and water in a combined amount of at least 50% by weight of the biocidal composition. Suitably, the biocidal composition comprises one or more phosphonium compound(s), one or more oxazolidine compound(s) and water in a combined amount of at least 90% by weight of the biocidal composition. Suitably, the biocidal composition comprises one or more phosphonium compound(s), one or more oxazolidine compound(s) and water in a combined amount of at least 95% by weight of the biocidal composition, for example at least 99% by weight. Suitably, the biocidal composition consists of one or more phosphonium compound(s), one or more oxazolidine compound(s) and water.

Suitably, the biocidal composition comprises a phosphonium compound in an amount of at least 1% by weight. The biocidal composition may comprise a phosphonium compound in an amount of at least 2% by weight, for example at least: 3%; 4% or 5% by weight.

Suitably, the biocidal composition comprises am oxazolidine compound in an amount of at least 1% by weight. The biocidal composition may comprise an oxazolidine compound in an amount of at least 2% by weight, for example at least: 3%; 4% or 5% by weight. The biocidal composition may comprise an oxazolidine compound in an amount of at least 10% by weight, for example at least: 15%; 20%; 25% or 30% by weight. The biocidal composition may comprise an oxazolidine compound in an amount of at least 35% by weight, for example at least: 40%; 45%; 50%; 55%; 60%; 65% or 70% by weight.

Suitably, the biocidal composition comprises a phosphonium compound (a) and a oxazolidine compound (b) in a weight ratio, expressed as active compound, of phosphonium compound:oxazolidine compound of from 1.0:0.5 to 1.0:100.0, for example from 1.0:1.0 to 1.0:50.0.

Suitably, the biocidal composition comprises a phosphonium compound (a) and a oxazolidine compound (b) in a weight ratio, expressed as active compound, of phosphonium compound:oxazolidine compound of from 1.0:2.0 to 1.0:20.0, for example from 1.0:3.0 to 1.0:15.0.

Suitably, the phosphonium compound (a) has formula:

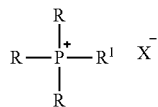

wherein each R is independently a $C_1$-$C_6$ alkyl group which is unsubstituted or substituted by a cyano, hydroxyl, esterified hydroxyl or aryl group;

$R^1$ represents a $C_8$-$C_{18}$ alkyl group which is substituted or unsubstituted; and X represents either chlorine or bromine.

Suitably, each R is a $C_1$-$C_6$ alkyl group. Suitably, each R is a $C_3$-$C_5$ alkyl group. Suitably each R is a butyl group.

Suitably $R^1$ represents a $C_8$-$C_{18}$ alkyl group. Suitably, R1 is a $C_{12}$-$C_{16}$ alkyl group. Suitably, $R^1$ is a tetradecyl group.

Suitably, X is chlorine.

Suitably, the phosphonium compound (a) is a phosphonium chloride.

Suitably, said compound (a) comprises TTPC.

The biocidal composition may comprise a combination of oxazolidine compounds (b). Suitably, the biocidal composition comprises a single type of oxazolidine compounds (b).

Suitably, the oxazolidine compound (b) is selected from the group consisting of oxazolidines and oxazolidine derivatives. Suitably, the oxazolidine compound (b) comprises an oxazolidine. Suitably, the oxazolidine compound (b) consists of an oxazolidine. Suitably, the oxazolidine compound (b) comprises an oxazolidine derivative. Suitably, the oxazolidine compound (b) consists of an oxazolidine derivative.

Suitably, the oxazolidine compound (b) comprises a methyloxazolidine. Suitably, the oxazolidine compound (b) consists of a methyloxazolidine. Suitably, the oxazolidine compound (b) comprises a dimethyloxazolidine. Suitably, the oxazolidine compound (b) consists of a dimethyloxazolidine.

Suitably, the oxazolidine compound (b) comprises 4,4-dimethyloxazolidine. Suitably, the oxazolidine compound (b) consists of 4,4-dimethyloxazolidine.

Suitably, TTPC comprises greater than 50% of the total phosphonium compound(s) in the biocidal composition. Suitably, TTPC comprises greater than 90% of the total phosphonium compound(s) in the biocidal composition, for example 99% or greater.

Suitably, 4,4-dimethyloxazolidine comprises greater than 50% of the total oxazolidine compound(s) in the biocidal composition. Suitably, 4,4-dimethyloxazolidine comprises greater than 90% of the total oxazolidine compound(s) in the biocidal composition, for example 99% or greater.

Suitably, there is provided a biocidal composition comprising a combination of:

(a) tri n-butyl n-tetradecyl phosphonium chloride (TTPC); and (b) 4,4-dimethyloxazolidine (DMO).

The biocidal composition of the sixth aspect may comprise any feature as described in relation to one or more of the first and/or second and/or third and/or fourth and/or fifth aspects except where such features are mutually exclusive.

DETAILED DESCRIPTION OF PREFERRED EMBODIMENTS

The present invention will now be illustrated by way of example with reference to the following preferred embodiments.

Examples

Aqueous systems inoculated with anaerobe and facultative anaerobe culture and having a total dissolved solids (TDS) concentration of 30,000 mg $l^{-1}$ were prepared and treated with treatment agents comprising: (a) a phosphonium compound and (b) an oxazolidine compound. The phosphonium compound (a) used was tri n-butyl n-tetradecyl phosphonium chloride (TTPC). The oxazolidine compound (b) was 4,4-dimethyloxazolidine (DMO).

TTPC was used in the form of Bellacide 350, an aqueous composition of TTPC and water consisting of water and 50% by weight of TTPC available from BWA Water Additives.

DMO was used in the form of Mergal 192 a 73.7% aqueous solution of DMO available from Troy Chemical Corporation.

A suspension of *Desulfovibrio vulgaris* plus *Enterobacter aerogenes* bacteria containing from $1 \times 10^5$ to $1 \times 10^6$ cells/mL was prepared in sterile pH 8 phosphate buffer containing sodium chloride to give the desired total dissolved solids (TDS) concentration. Aliquots of this suspension were dosed with the indicated concentrations of the compounds (a) and (b) with the concentrations being measured as ppm active. The mixtures were allowed to stand at room temperature. At the designated contact times, each mixture was sampled to determine the total number of viable cells of both *Desulfovibrio vulgaris* and *Enterobacter aerogenes* by serial 10-fold dilution into API RP 38 media vials and anaerobic acid producing media vials, respectively. The vials were incubated at 37° C. for 72 hours. Results were recorded as $\log_{10}$ reduction in the viable count versus the control.

The efficacy of the treatment agents was evaluated by measuring the $\text{Log}_{10}$ Reduction of the anaerobic bacterium *Desulfovibrio vulgaris* and the facultative anaerobic bacterium *Enterobacter aerogenes* after contact times of 1 hour, 4 hours and 24 hours as detailed in Table 1. For TTPC the stated ppm value relates to the amount of TTPC added (active). For the 4,4-dimethyloxazolidine the stated ppm relates to the amount of 4,4-dimethyloxazolidine added (active).

TABLE 1

| Example | TDS (mg l⁻¹) | Contact time (hours) | Treatment agent (ppm active) TTPC | Treatment agent (ppm active) DMO | Log₁₀ Reduction Anaerobes* | Log₁₀ Reduction Facultative Anaerobes* |
|---|---|---|---|---|---|---|
| 1 | 30,000 | 1 | 3.125 | — | 1 | 1 |
| 2 | 30,000 | 1 | 6.25 | — | 2 | 3 |
| 3 | 30,000 | 1 | — | 40 | 1 | 0 |
| 4 | 30,000 | 1 | — | 80 | 1 | 0 |
| 5 | 30,000 | 1 | 3.125 | 40 | 5 | 2 |
| 6 | 30,000 | 1 | 6.25 | 40 | 5 | 4 |
| 7 | 30,000 | 4 | 3.125 | — | 5 | 2 |
| 8 | 30,000 | 4 | 6.25 | — | 5 | 4 |
| 9 | 30,000 | 4 | — | 40 | 1 | 0 |
| 10 | 30,000 | 4 | — | 80 | 2 | 0 |
| 11 | 30,000 | 4 | 3.125 | 40 | 5 | 2 |
| 12 | 30,000 | 4 | 6.25 | 40 | 5 | 6 |
| 13 | 30,000 | 24 | 3.125 | — | 5 | 4 |
| 14 | 30,000 | 24 | 6.25 | — | 5 | 5 |
| 15 | 30,000 | 24 | — | 40 | 1 | 0 |
| 16 | 30,000 | 24 | — | 80 | 2 | 0 |
| 17 | 30,000 | 24 | 3.125 | 40 | 5 | 8 |
| 18 | 30,000 | 24 | 6.25 | 40 | 5 | 8 |

*5 = complete kill for anaerobes
*8 = complete kill for facultative anaerobes

The results show that surprisingly, despite TTPC and DMO each being relatively ineffective alone against anaerobes at short contact times, the combination of TTPC and DMO was very effective against anaerobes achieving complete kill (5 log reduction) at one hour compared to a 1-2 log reduction at the same concentrations of TTPC or DMO when used individually.

The results with facultative anaerobes, also show unexpected efficacy of the combination of TTPC and DMO with the combination achieving complete kill (8 log reduction) at 24 hours.

Accordingly, it will be appreciated that combining TTPC and DMO may allow for less DMO or TTPC to be used to achieve kill of facultative anaerobes and anaerobes compared to TTPC or DMO alone. It will also be appreciated that combining TTPC and DMO may allow for complete kill of facultative anaerobes and anaerobes using TTPC and DMO at certain contact times which may not be achievable if using only DMO or TTPC.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of treating an aqueous system having a total dissolved solids (TDS) of 1000 mg l⁻¹ or greater to inhibit growth of one or more micro-organisms therein and/or to reduce the number of live micro-organisms therein, wherein the method comprises adding treatment agents to said aqueous system and wherein said treatment agents comprise:
   (a) a tetra alkyl phosphonium compound having formula:

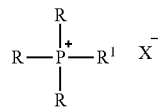

wherein each R is independently a $C_1$-$C_6$ alkyl group; $R^1$ represents a $C_8$-$C_{18}$ alkyl group; and X represents either chlorine or bromine; and
   (b) an oxazolidine compound.

2. A method according to claim 1, wherein the tetra alkyl phosphonium compound (a) comprises tri n-butyl n-tetradecyl phosphonium chloride (TTPC).

3. A method according to claim 1, wherein the oxazolidine compound (b) comprises 4,4-dimethyloxazolidine (DMO).

4. A method according to claim 1, wherein the method comprises treating an aqueous system to inhibit growth of facultative anaerobic bacteria and/or anaerobic bacteria and/or to reduce the number of live facultative anaerobic bacteria and/or anaerobic bacteria therein.

5. A method according to claim 1, wherein the method comprises treating an aqueous system having a total dissolved solids (TDS) of 10,000 mg l⁻¹ or greater.

6. A method according to claim 1, wherein the method comprises adding a tetra alkyl phosphonium compound (a) to an aqueous system in an amount of at least 1 part per million (ppm).

7. A method according to claim 1, wherein the method comprises adding an oxazolidine compound (b) to an aqueous system such in an amount of at least at least 1 part per million (ppm).

8. A method according to claim 1, wherein the method comprises adding a tetra alkyl phosphonium compound (a) and an oxazolidine compound (b) to an aqueous system in a weight ratio, expressed as active compound, of tetra alkyl phosphonium compound:oxazolidine compound of from 1.0:1.0 to 1.0:50.0.

9. A method of treating an aqueous system having a total dissolved solids (TDS) of 1000 mg l⁻¹ or greater to inhibit growth of one or more micro-organisms therein and/or to reduce the number of live micro-organisms therein, wherein the method comprises adding treatment agents to said aqueous system and wherein said treatment agents comprise:
   (i) tri n-butyl n-tetradecyl phosphonium chloride (TTPC); and
   (ii) 4,4-dimethyloxazolidine (DMO).

10. A method according to claim 9, wherein the method comprises treating an aqueous system and wherein the method comprises adding TTPC to an aqueous system in an amount of at least 1 part per million (ppm) and adding 4,4-dimethyloxazolidine to an aqueous system in an amount of at least 1 part per million (ppm).

11. A method according to claim 10, wherein the method comprises treating an aqueous system to inhibit growth of facultative anaerobic bacteria and/or anaerobic bacteria and/or to reduce the number of live facultative anaerobic bacteria and/or anaerobic bacteria therein.

12. A method according to claim 1, wherein the method employs a tetra alkyl phosphonium compound (a) having formula:

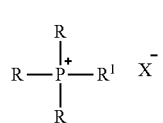

wherein each R is independently a $C_3$-$C_5$ alkyl group;
$R^1$ represents a $C_{12}$-$C_{16}$ alkyl group; and
X represents either chlorine or bromine.

* * * * *